US00PP10745P

United States Patent [19]

Nicolai

[11] Patent Number: Plant 10,745

[45] Date of Patent: Jan. 5, 1999

[54] APPLE TREE NAMED 'M9-RN8'

[75] Inventor: René Nicolai, Alken, Belgium

[73] Assignee: Renee Nicolai N.V. Fruitboomwekerij, Belgium

[21] Appl. No.: 995,334

[22] Filed: Dec. 22, 1992

Related U.S. Application Data

[63] Continuation of Ser. No. 642,911, Jan. 18, 1991, abandoned.

[51] Int. Cl.[6] ..... A01H 5/00

[52] U.S. Cl. ..... Plt./34.1

[58] Field of Search ..... Plt./34.1, 35.1, Plt./35.2

[56] References Cited

PUBLICATIONS

Anon. *Stark Bro's Fruit* Tree *Catalog & Guide for the Professional Grower* 1989 Stark Bro's Nursery and Orchards Co., Louisana, Mo. pp. 18 and 19.

Anon. *Oregon Rootstock, Inc. Catalog* 1985, Oregon Rootstock, Inc., Woodburn, Oregon. pp. 8–15.

Tukey, H.B., "Dwarfing Rootstocks for Apple" Dwarfed *Fruit Trees* The Macmillian Co., N.Y. 1964 pp. 123–154.

von Oosten, H.J., et al., "Differences Between Subvarieties of 'M.9'" *De Fruitteelt* (English Translation) (all 1984) No. 32, pp. 924–926; No. 33, pp. 950–951; No. 34, pp. 968–969; and, No 35, pp. 988–989.

Masseron, A., "Study and Selection of Paradise Jaune De Metz (English Translation) Rootstock of the Apple Tree" Interprofessional Technical Center for the Fruits and Vegatables, CTIFL, Service for Improving Production, Domaine de Laxade, Prigonrieux 24130 La Force, pp. 35–57 (With Pages Missing in Between).

Ziebig, R., et al., "Autonomous Province Bozen—South Tyrol, Division VI, Agriculture and Forestry. 1992 Activity Program for the Agriculture and Forestry Experimental Center" Autonomous Province Bozen—South Tyrol, Division IV, Agriculture and Forestry. (English Translation of Document Provided by Applicant).

*Primary Examiner*—Howard J. Locker

*Attorney, Agent, or Firm*—Chernoff, Vilhauer McClung & Stenzel, LLP

[57] ABSTRACT

This invention relates to a new and distinct apple tree rootstock clone which is useful as a size-controlling rootstock. The new clone originated as a mutation of Malling 9 (M9), an unpatented dwarfing apple rootstock, Standard growing apple cultivars propagated on this new rootstock are approximately 70 % of the size of like apple trees growing on apple seedling rootstocks. In the stoolbed the clone produces few lateral limbs, large round to oval leaves with broadly acute tips and possesses a pronounced, profuse blooming characteristic. The clone produces a larger number of rooted plants in the stoolbed.

5 Drawing Sheets

BACKGROUND AND SUMMARY OF THE INVENTION

The subject clone is a sport of Malling 9 MM9), an unpatented apple rootstock clone. The original plant was selected as a mutation in 1967 from a large stoolbed of M9 plants. The stoolbed had been planted in 1960 and was growing in the Rene Nicolai nursery, Linderstroot, 22-B-3820 Alken, Belgium. The original source of the bed was the East Malling Research Station in England. The clone was one of a group of clones that were selected by Mr. Nicolai and other rootstock specialists for their differences in lateral branching, leaf development and shape, leaf color, thickness of the shoots, rooting ability in the stoolbed, bloom characteristics and other noticed differences from the mother stoolbed plants.

Following its selection, the clone was assigned a number (RN8) and was propagated for further testing and evaluation.

Since all original M9 rootstocks have been found to be virus infected, RN8 stocks were subsequently heat-treated by application of dry heat in order to obtain virus-free specimens. After heat treatment and subsequent virus testing, the new rootstock clone was again exposed to multiplication techniques (stooling) followed by continued testing and evaluation.

Virus-free RN8 progeny plants were expanded into small stoolbed plantings which were planted separately rately in order to examine the new rootstocks's individual characteristics in small semi-commercial stoolbed sites.

These small experimental stoolbeds of RN8 were established for such further evaluations as follows:

1. A site at Deveaux, Belgium was planted in the spring of 1974 with 555 plants of the subject clone.

2. A site at Bordeaux, France was planted in 1977 with 200 plants of the subject clone.

3. A site at Wissenhoeve, Belgium was planted in the spring of 1980 with 1,176 plants of the subject clone.

4. A site near St. Truiden, Belgium was planted in the spring of 1982 wtih 100 plants of the suject clone.

5. A site at Henkaenrts, Belgium was planted in the spring of 1986 with 4,600 plants of the subject clone.

6. A site at Ephrata, was planted in the spring of 1990 with 2,000 plants of the subject clone.

Clone RN8 was subsequently finally selected as a rootstock clone that continues to possess growth and rooting characteristics that are distinctly different from its M9 parent.

It distinguished itself in these beds from its M9 parent in the following ways:

1. The subject clone produces fewer lateral limbs (feathers) than its M9 parent. At the Bordeaux test site in France and at the Ephrata, Wash. site, feathers produced were about one half the number produced on its M9 parent (FIGS. 1 and 2; Tables 1 and 2). RN8 grows less robustly in the stoolbed and exhibits a shorter, stockier growth characteristic when compared to its M9 parent (FIG. 4, M9; and FIG. 5, RN8).

Nodes are spaced closer together on shoots and average stem circumference is significantly more than the average stem Circumference of M9 (Table 2). The average length of feathers on RN8 was slightly less than the average length of feathers on its M9 parent (Table 2).

TABLE 1

Percent of Layer Plants with Side Limbs (Feathers)
(Test Stooling Beds at Bordeaux, France)

| Rootstock | Year | | | | |
|---|---|---|---|---|---|
| Clone | 79/80 | 80/81 | 81/82 | 82/83 | Average |
| M9 (virus-free) | 13 | 8 | 25 | 0 | 11.5 |
| RN8 | 8 | 6 | 13 | 0 | 6.8 |
| RN19 | 41 | 32 | 44 | 19 | 34.0 |
| RN29 | 39 | 22 | 35 | 15 | 27.8 |

TABLE 2

Growth Characteristics
(Test Stooling Beds at Ephrata, Washington)

| Rootstock Clone | Length of Shoot (cm) | Number of Nodes/ Shoot | Number of Spurs/ Shoot | Length of Spur (cm) | Number of Leaves/ Shoots | Circumference of Stem (cm) |
|---|---|---|---|---|---|---|
| M9 | 66.80* | 39.20 | 3.00 | 1.50 | 53.00 | 3.24 |
| RN8 | 62.10 | 42.10 | 1.80 | 1.20 | 57.20 | 3.80 |
| RN19 | 78.20 | 41.00 | 18.60 | 8.60 | 88.30 | 3.51 |
| RN29 | 86.20 | 45.60 | 21.40 | 10.30 | 100.00 | 3.54 |

*All numbers shown are the average of 100 plants selected at random.

2. Leaves of the subject clone are larger and more rounded in shape and leaf margins are more sinuate than those of M9. Leaves of RN8 are round to oval in shape with broadly acute tips. Theis leaf characteristic is very pronounced in the older leaves (FIG. 3; Table 3).

TABLE 3

Leaf Size and Respetive Petiole
Length of Respective Rootstock
(Test Stooling Beds at Bordeaux, France)

| Rootstock Clone | Length, L (mm) | Width, W (mm) | L + W (mm) | Length of Petiole |
|---|---|---|---|---|
| M9 (virus-free) | 101.7 | 63.8 | 165.5 | 32.5 |
| RN8 | 98.8 | 73.6 | 172.4 | 34.0 |
| RN19 | 91.4 | 60.0 | 151.4 | 30.8 |
| RN29 | 85.5 | 57.1 | 142.6 | 28.5 |

3. The profuse blooming characteristic of RN8 is very pronounced and in this respect differs distinctly from its M9 parent. The number of blooms produced on RN8 two-year-old line-out stocks was about two-fold that of its M9 parent (Table 4).

TABLE 4

Bloom Characteristics
(Research Station at Gorsum, Belgium - 1985)

| Rootstock Clone | % of Rootstocks With Bloom (1 Year From Stoolbed) |
|---|---|
| RN8 | 29 |
| RN19 | 4 |
| RN29 | 0 |
| M9 (virus-free) | 15 |

4. Rooting ability (number and quantity of roots produced per length of stoolbed shank) of the subject clone is significantly more than that demonstrated strated by its M9 parent. Also, the average number of rooted plants produced per stoolbed mother plant and/or per meter of stoolbed row is significantly more than the average produced by M9 mother stocks (Table 5 , 6 and 7). This difference in number of rooted daughter plants was approximately two-fold at the test site near Bordeaux, France after five years in the stoolbed (Table 7). These characteristics are stable and have been transmitted without change through succeeding generations.

TABLE 5

RN8 Stoolbed Production (Deveaux, Belgium)
No. Mother Plants - 555
Length of Bed (m) - 185

| Year | 82/83 | 83/84 | 84/85 | 85/86 | 86/87 |
|---|---|---|---|---|---|
| Grade (mm) | | | | | |
| 10/12 | 300 | 150 | 150 | 1,100 | 500 |
| 8/10 | 0 | 0 | 700 | 0 | 0 |
| 6/10 | 4,650 | 3,350 | 0 | 0 | 2,800 |
| 6/8 | 0 | 0 | 3,700 | 3,100 | 0 |
| 5/7 | 0 | 0 | 0 | 0 | 0 |
| 4/6 | 2,400 | 1,800 | 3,200 | 1,900 | 3,900 |
| 04 | 0 | 600 | 0 | 0 | 0 |
| #2s | 1,000 | 1,400 | 600 | 900 | 1,900 |
| Totals | 8,350 | 7,300 | 8,350 | 7,000 | 9,100 |
| Per Mother Plant | 15.05 | 13.15 | 15.05 | 12.61 | 16.40 |
| Per Meter | 45.14 | 39.46 | 45.14 | 37.84 | 49.19 |

| Year | 87/88 | 88/89 | 89/90 | 90/91 | Average 82/91 |
|---|---|---|---|---|---|
| Grade (mm) | | | | | |
| 10/12 | 675 | 200 | 0 | 0 | |
| 8/10 | 925 | 1,925 | 850 | 2,225 | |
| 6/10 | 0 | 0 | 0 | 0 | |
| 6/8 | 3,300 | 2,700 | 3,000 | 0 | |
| 5/7 | 0 | 0 | 0 | 3,450 | |
| 4/6 | 2,700 | 1,200 | 3,400 | 1,600 | |
| 04 | 0 | 0 | 0 | 0 | |
| #2s | 1,300 | 1,100 | 3,400 | 700 | |
| Totals | 8,900 | 7,125 | 10,650 | 7,975 | |
| Per Mother Plant | 16.04 | 12.84 | 19.19 | 14.37 | 14.96 |
| Per Meter | 48.11 | 38.51 | 57.57 | 43.11 | 44.89 |

TABLE 6

M9 (Virus-Free) Stoolbed Production (Deveaux, Belgium)
No. Mother Plants - 561
Length of Bed (m) - 187

| Year | 82/83 | 83/84 | 84/85 | 85/86 | 86/87 |
|---|---|---|---|---|---|
| Grade (mm) | | | | | |
| 10/12 | 225 | 100 | 250 | 750 | 464 |
| 8/10 | 0 | 0 | 450 | 0 | 0 |
| 6/10 | 4,150 | 2,950 | 0 | 2,350 | 2,200 |
| 6/8 | 0 | 0 | 3,400 | 0 | 0 |
| 5/7 | 0 | 0 | 0 | 0 | 0 |
| 4/6 | 1,800 | 1,600 | 2,200 | 1,600 | 3,000 |
| 04 | 0 | 300 | 0 | 0 | 0 |
| #2s | 700 | 800 | 500 | 500 | 1,400 |
| Totals | 6,875 | 5,750 | 6,800 | 5,200 | 7,064 |
| Per Mother Plant | 12.25 | 10.25 | 12.12 | 9.27 | 12.59 |
| Per Meter | 36.76 | 30.75 | 36.36 | 27.81 | 37.78 |

| Year | 87/88 | 88/89 | 89/90 | 90/91 | Average 82/91 |
|---|---|---|---|---|---|
| Grade (mm) | | | | | |
| 10/12 | 75 | — | — | — | |
| 8/10 | 450 | — | — | — | |
| 6/10 | 0 | — | — | — | |
| 6/8 | 2,700 | — | — | — | |
| 5/7 | 0 | — | — | — | |
| 4/6 | 2,200 | — | — | — | |
| 04 | 0 | — | — | — | |
| #2s | 400 | — | — | — | |
| Totals | 5,825 | — | — | — | |
| Per Mother Plant | 10.38 | — | — | — | 11.14 |
| Per Meter | 31.15 | — | — | — | 33.43 |

TABLE 7

Average Number of Plants Per Stoolbed Mother Plant
(Test Stooling Beds at Bordeaux, France)

| Rootstock Clone | Year Planted and Age 79/80 2-Yr | 80/81 3-Yr | 81/82 4-Yr | 82/83 5-Yr | Average |
|---|---|---|---|---|---|
| M9 (virus-free) | 1.2 | 2.6 | .5 | 4.0 | 8.3 |
| RN8 | 2.1 | 3.9 | 3.8 | 6.4 | 16.2 |
| RN19 | 2.6 | 4.4 | 6.5 | 9.1 | 22.6 |
| RN29 | 4.4 | 5.6 | 5.7 | 11.3 | 27.0 |

BRIEF DESCRIPTION OF THE DRAWINGS

Since the subject clone is intended to be used only as rootstock for apple cultivar, the drawings center on the vegatative parts rather than the flowers and fruits.

DESCRIPTION OF VEGATATIVE CHARACTERISTICS

Figure 1:
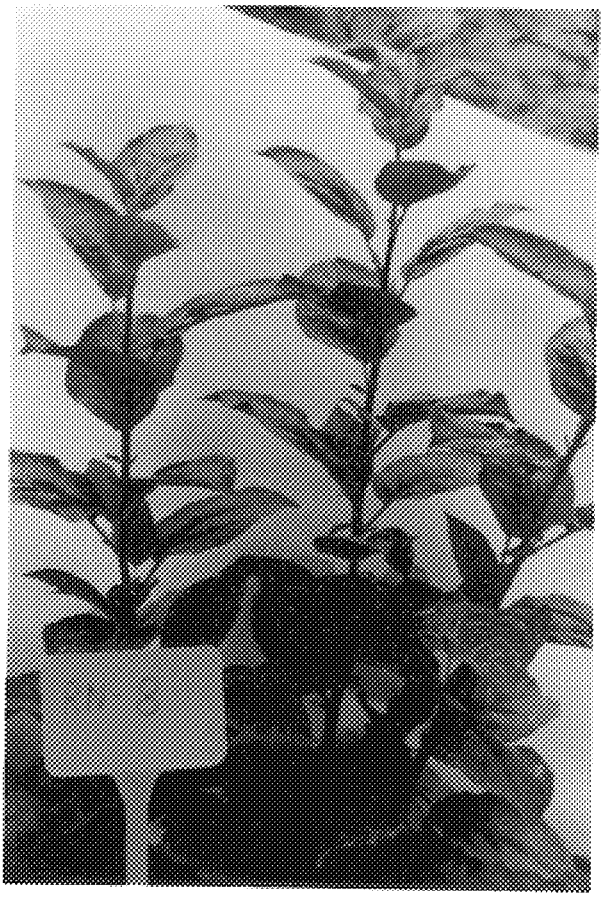
FIGS. 1 and 2 show the absence of lateral brancess (feathers) on daughter stoolbed plants.
Figure 2:
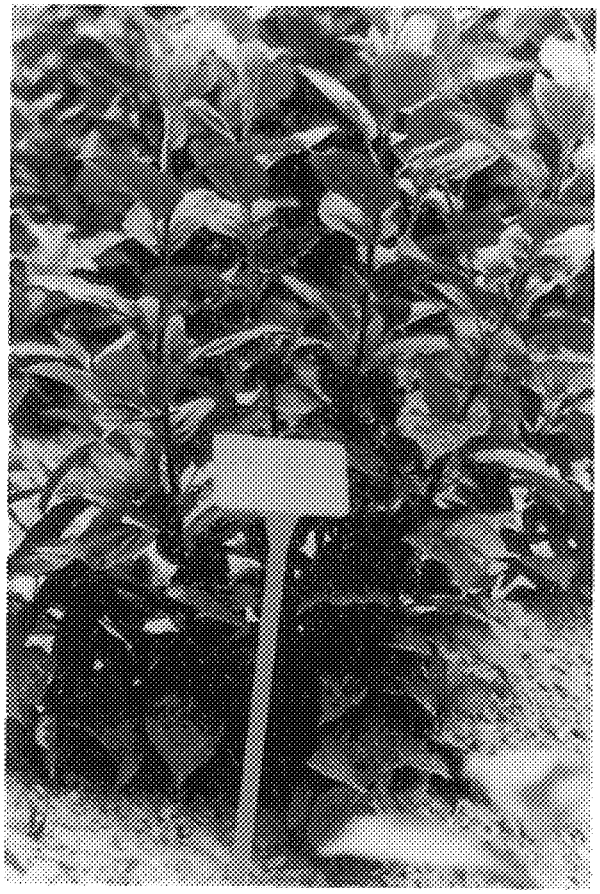
Figure 3:
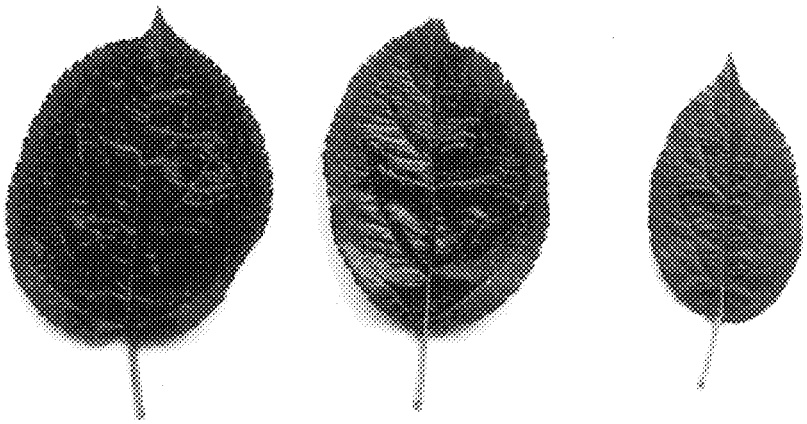
FIG. 3 shows the round- to oval-shaped leaves, broadly acute tips and sinuate leaf serration.
Figure 4:
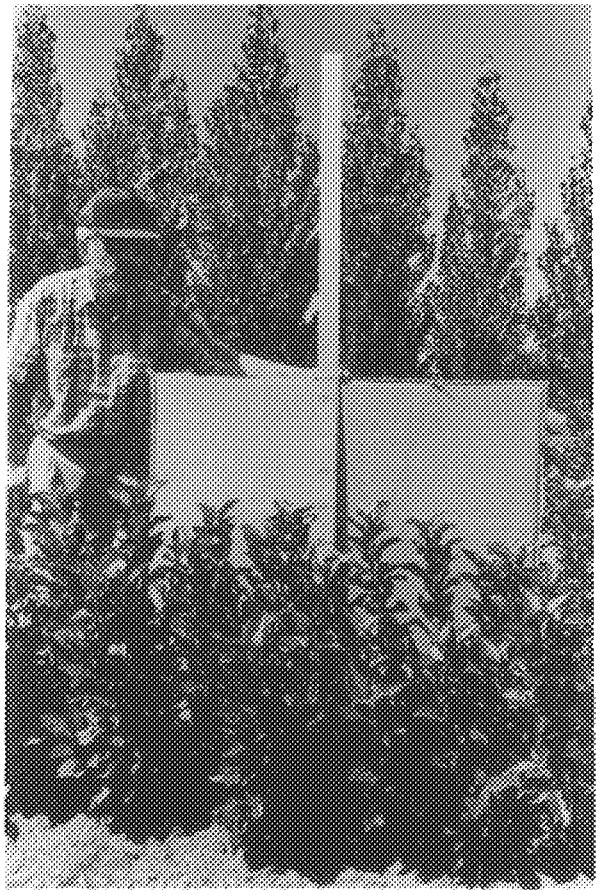
FIG. 4 shows the average height in centimeters of M9 rootstock daughter plants in a stoolbed row in Ephrata, Wash.
Figure 5:
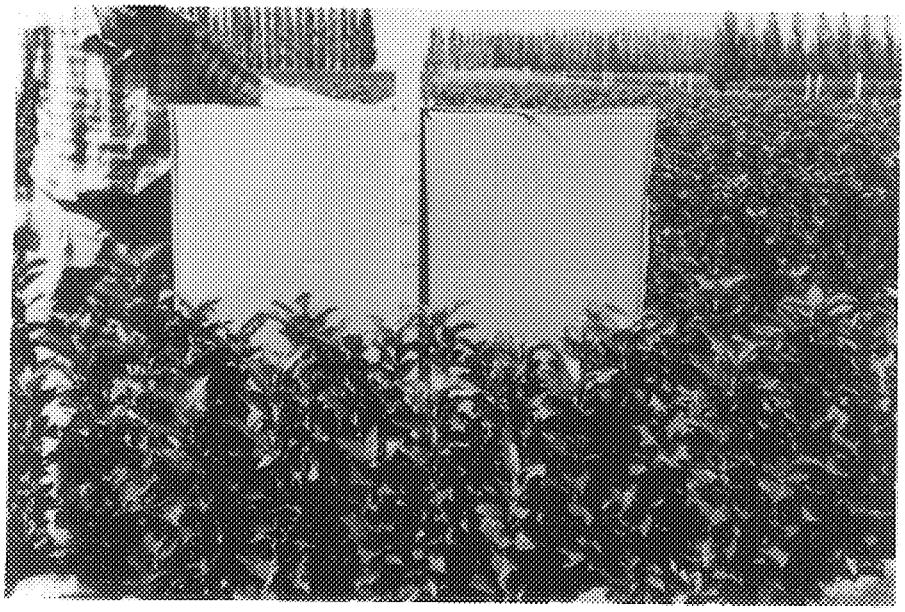
FIG. 5 shows the average height in centimeters of RN8 rootstock daughter plants in a stoolbed row in Ephrata Wash.

The following is a detailed description of the new apple rootstocks growth characteristics based on the stoolbed plants grown at the six test sites described above. Colors of the leaves and shoots are based on their appearance at the sites where grown. In those instances where a precise color assessment can be made, reference is to the Munsell Limit Color Cascade Table. In other instances, general color terms are used in accordance with the ordinary dictionary significance.

General habit:
- *Strength of growth.*—Vigorous, stiff.
- *Habit.*—Upright.
- *Branching.*—Very few, flexible.

Vegatative Shoots:
- *Bark color.*—Greenish-brown (21-15).
- *Pubescence.*—Very finely tomentose.
- *Lenticels.*—Few, inconspicuous, widely spaced, small, white.

Leaves:
- *Size.*—7.4 cm wide, 10.0 cm long.
- *Shape.*—Oval to round, slightly asymmetric.
- *Base.*—Obtuse, attenuated.
- *Apex.*—Broadly acute.
- *Serrations.*—Sinuate at sides, very obtuse to lacking at base.
- *Spacing.*—Normal phyllotaxical arrangement for Malus.
- *Color.*—Light green (22-14) with pinkish tips.

Leaf scars:
- *Shape.*—Broad V, slightly raised.
- *Color.*—Brown.

Petioles:
- *Shape.*—Slender, slightly channeled.
- *Length.*—Medium, 3.4 cm.
- *Color.*—Reddish-brown (32-12).
- *Pose.*—Acute angle near tip, slightly acute to horizontal along sides.
- *Glands.*—None.

Stipules:
- *Size.*—Small, 3.5-5 mm, inconspicuous, minutely serrated.
- *Color.*—Light green.
- *Pose.*—Mostly reposed along petiole.

Lateral buds:
- *Size.*—Small.
- *Shape.*—Flat, angular.
- *Color.*—Dark brown.
- *Pubescence.*—Finely tomentose.

Apical buds:
- *Size.*—Larger than lateral buds.
- *Shape.*—Obtuse.
- *Color.*—Dark brown.
- *Pubescence.*—Tomentose.

Dormant Plant

Shoots:
- *Size.*—Stocky, 6–10 mm in caliper at base, stiff, brittle.
- *Bark Color.*—Dark brown (25-15-1 ).
- *Pubescence.*—Conspicuously pubescent.
- *Nodes.*—Larger in diameter than internodes with slight shoulder at each side on leaf scar.
- *Internodes.*—Smooth, regularly spaced.

Stooling and Root Characteristics

Rooting and stooling: Multiplies well in stoolbeds, forming strong roots along full length of shank. Roots arise from nodes.

Habit of growth in stoolbed: Shoots arise from nodes, grow mostly outward at a slight angle.

Flower Characteristics

Flowers:

*Size.*—3.5 cm in diameter.

*Color.*—White with pink streaks at base.

Fruit:No commercial value, but useful for identification. No

*Shape.*—Round to slightly oblong.

*Color.*—Red Stripes.

*Size.*—About 4.5 cm in diameter and about 5.5 cm in length.

*Flavor.*—Bland, tasteless.

General Characteristics

Rootsuckering: Few rootsuckers.

Size control potential: Size of trees budded on the subject rootstocks will vary according to the vigor of the cultivar and/or type of soil and orchard management. "Standard" growing cultivars such as Red and Golden Delicious are reduced in size about 70% when compared to apple seedling rootstocks. Less vigorous varieties are more reduced in size and more vigorous varieties are less reduced in size.

Dwarfing: Fully dwarfing.

Precocity: Varies according to variety, most cultivars often flower and set fruit the first year in the orchard and thereafter bear fruit each year.

Compatibility: Graft compatible with all major commerical fruiting varieties.

Root Anchorage: Needs support.

Hardiness: Hardy in most commercial apple growing areas.

Disease and pest resistance: Average resistance to common diseases and pests of apple. Tested and found free of all known virus diseases to apple.

What is claimed is:

1. A new and distinct apple tree clone, a sport of the Malling 9, referred to by the cultivar designation 'M9-RN8', substantially as herein shown and described, characterized particularly by its ability to serve as a rootstock for grafting of apple tree cultivars to produce dwarf apple trees and by its ability to rot very readily in the stoolbed with very little lateral branching and produce high quality stoolbed rootstock plants for nursery use.

* * * * *

RN-8